United States Patent
Joos

(10) Patent No.: US 6,554,867 B1
(45) Date of Patent: Apr. 29, 2003

(54) SURFACE STRUCTURE FOR INTRAOSSEOUS IMPLANT

(75) Inventor: Ulrich Joos, Münster (DE)

(73) Assignee: Lipat Consulting AG, Basel (CH)

( * ) Notice: Subject to any disclaimer, the term of this patent is extended or adjusted under 35 U.S.C. 154(b) by 0 days.

(21) Appl. No.: 09/869,781

(22) PCT Filed: Jan. 12, 1999

(86) PCT No.: PCT/CH99/00010
§ 371 (c)(1),
(2), (4) Date: Jul. 5, 2001

(87) PCT Pub. No.: WO99/13700
PCT Pub. Date: Mar. 25, 1999

(51) Int. Cl.$^7$ .................................................. A61F 2/28
(52) U.S. Cl. .................................................. 623/23.5
(58) Field of Search .......................... 623/11.11, 16.11, 623/23.29, 23.5, 23.31; 433/201.1

(56) References Cited

U.S. PATENT DOCUMENTS

| | | |
|---|---|---|
| 4,865,603 A | 9/1989 | Noiles |
| 4,865,608 A | 9/1989 | Brooker, Jr. |
| 5,573,401 A * | 11/1996 | Davidson et al. ......... 433/201.1 |
| 5,645,740 A * | 7/1997 | Naiman et al. ......... 219/121.68 |

FOREIGN PATENT DOCUMENTS

| | | |
|---|---|---|
| EP | 0388576 | 9/1990 |
| EP | 0639356 | 2/1995 |
| EP | 0669116 | 8/1995 |
| GB | 2045083 | 10/1980 |
| WO | 9509583 | 4/1995 |
| WO | 9728760 | 8/1997 |
| WO | 9746179 | 12/1997 |

OTHER PUBLICATIONS

Schroeder, A., et al., Orale Implantologie (Oral Implantology), Georg Thieme Verlag, Stuttgart, 2nd Edition, 1994, pp. 48–59.

Könönen, M., et al., "Effect of surface processing on the attachment, Orientation, and proliferation of human gingival fibroblasts on titanium", Journal of Biomedical Materials Research, vol. 26, 1992, pp. 1325–1341.

Woods, A., et al., "Stages in specialization of fibroblast adhesion and deposition of extracellular matrix", European Journal of Cell Biology (32), 1983, pp. 108–116.

Dunn, G. A., et al., "A new hypothesis of contact guidance in tissue cells", Experimental Cell Research (101), 1976, pp. 1–14.

* cited by examiner

Primary Examiner—Jeffrey A. Smith
(74) Attorney, Agent, or Firm—Selitto, Behr & Kim

(57) ABSTRACT

The intraosseous implant intended to be fitted in a bone is provided on the surface with a specific roughness, the implant surface having depressions (1) with a depth (c) of about 20 $\mu$m to about 60 $\mu$m. At the bottom of the depressions (1) there are base faces (2), and between the depressions (1) there are plateau faces (3). Base faces (2) and plateau faces (3) have a horizontal extent (a, b) of about 10 $\mu$m to about 20 $\mu$m. These depressions (1) are ideally as smooth as possible, i.e. they have no surface roughness below the cellular dimension. Obliquely ascending side faces (4) extend from the base faces (2) to the plateau faces (3), and the angle of inclination ($\alpha$) between the horizontal and the side faces (4) is about 30° maximum. Below the upper neck portion, the implant has a self-tapping thread, and the neck portion of the implant is provided with a porcelain-like coating. The surface energy and surface tension of the implant are kept as low as possible. Materials which can preferably be used for the implants are titanium, titanium-based alloys or porcelain-like substances. The surface structure results in an implant which, while providing sound immediate postoperative primary stability, is also distinguished by an accelerated and increased load-bearing capacity on account of more intensive osseointegration.

8 Claims, 1 Drawing Sheet

SURFACE STRUCTURE FOR INTRAOSSEOUS IMPLANT

FIELD OF THE INVENTION

Figure 1:
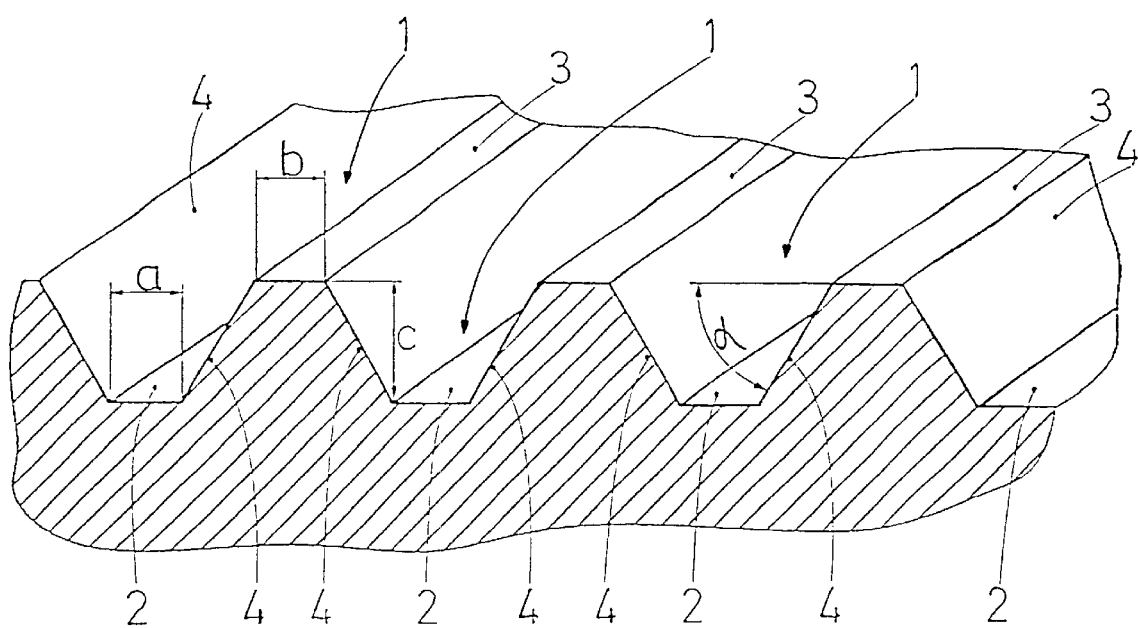

The invention relates to an implant to be surgically fitted in bone, preferably human bone, and covers for example the areas of osteosynthesis, prosthetics (in surgery of the hands, feet, hips and limbs), and maxillofacial and dental implantology. The invention in particular concerns the design of the implant and of its surface for the purpose of achieving immediate primary stability and rapid osseointegration.

PRIOR ART

There are two requirements regarding the stability of an implant:
a) an as far as possible immediate postoperative load-bearing capacity, i.e. immediate primary stability, which is based solely on mechanical principles; and
b) as rapid as possible secondary stability by means of osseointegration, which follows biological principles.

Apart from the quality of implantation and the local conditions in the area surrounding the implantation site, it has been recognized that a critical factor regarding the primary stability of the implant is its design, and that an outer screw thread delivers the best results for immediate stability. By contrast, osseointegration is crucially dependent on the choice of material (titanium and titanium-based alloys and porcelain-like substances are being increasingly used in this connection) and on the surface characteristics of the implant.

In GB-A-2,045,083, a surface roughness of the order of 0.01 μm to 0.3 μm is recommended. EP-B-0,388,576 proposes an ideal implant surface with a macro-roughness of more than 10 μm, preferably more than 20 μm, on which a micro-roughness of the order of 2 μm and finer is superimposed. Treating the implant surface with an abrasive is proposed in order to generate the macro-roughness, and etching in acid is proposed in order to generate the micro-roughness. WO-A-97/28760 discloses, for osteosynthesis screws, a roughness value $R_t$ of ca. $\geq 10$ μm (maximum peak-to-valley height). According to Schroeder, A.; Sutter, F.; Buser, D.; Krekeler, G. (Orale Implantologie [Oral implantology], Georg Thieme Verlag, Stuttgart, $2^{nd}$ edition, 1994, pages 48 et seq.), a plasma coating with a layer thickness of ca. 20–40 μm and a peak-to-valley height of ca. 15 μm is applied to the implant surface in order to increase the surface and promote osseointegration. In general, specialists in this field are of the firm opinion that macro and micro roughnesses, particularly in combination, promote the anchoring of intraosseous implants in the bone.

U.S. Pat. No. 4,865,603 discloses prosthetic implants which have a surface with a structure. The structure comprises first and second depressions, the dimensions of the second depressions being in the range of 25% to 75% of the dimensions of the first depressions. The dimensions of the first depressions, in particular the width, are in the range of between 200 μm and 1000 μm, preferably between 300 μm and 700 μm, and consequently the dimensions of the second depressions lie in the range of 50 μm to 750 μm, preferably in the range of 75 μm to 525 μm. The depth of the first depressions and also of the second depressions lies in principle in the range of the dimension, in particular the width, of the respective depressions. The second depressions can be groove-shaped or diamond-shaped in configuration.

Although previous measures have brought some progress in terms of primary and secondary anchoring of intraosseous implants in bone implant sites, further improvements are nevertheless desired in order to increase the rate of success of the implants, shorten overall surgical procedure and thus impose less strain on the patient and ensure that the patient can return more quickly to a by and large normal lifestyle.

OBJECT OF THE INVENTION

In view of the aims set out above, it is an object of the invention to create, for intraosseous implants, a surface structure which gives a high degree of primary stability immediately following surgery and which promotes rapid and as intensive as possible biological osseointegration of the fitted implant.

SUMMARY OF THE INVENTION

The main features of the invention can be summarized as follows:

The intraosseous implant intended to be fitted in a bone is provided with a specific roughness on the surface, said implant surface having a multiplicity of depressions with a vertically measured depth of 20 μm to 60 μm, between which there are plateau faces. At the bottom of the depressions there are base faces, and side faces extend from the base faces to the plateau faces. The base faces and the plateau faces have a horizontal extent of in each case 10 μm to 20 μm. The depressions and the plateau faces are smooth, i.e. they have no surface roughness which although below the cellular dimension of osteogenetic cells is nevertheless in the same order of magnitude.

The side faces of the depressions preferably form an angle of inclination relative to the horizontal of about 30° maximum. The implant preferably has an upper neck portion, and below this upper neck portion, a self-tapping thread. The neck portion of the implant can be provided with a porcelain-like coating. The surface energy, or "zeta potential", and the surface tension of the implant are kept preferably as low as possible. Materials used for the implants are preferably titanium, titanium-based alloys or porcelain-like substances. The depressions are preferably designed as systematically trapezoid grooves extending parallel to one another, said grooves being generated mechanically.

By virtue of the invention, an implant is now available which, while providing sound immediate postoperative primary stability, is distinguished, on account of improved osseointegration in terms of the biological union of the bone and the implant surface, by an accelerated and increased load-bearing capacity in terms of secondary anchoring.

The intraosseous implant intended to be fitted in a bone is provided with a specific roughness on the surface, where said implant surface:
a) has a multiplicity of depressions with a vertically measured depth of about 20 μm to about 60 μm;
b) at the bottom of the depressions there are base faces, and between the depressions there are plateau faces, said base faces and plateau faces having a horizontal extent of about 10 μm to about 20 μm;
c) side faces extend from the plateau faces to the base faces; and
d) the depressions and the plateau faces are ideally as smooth as possible, that is to say they have no surface roughness below the cellular dimension.

The side faces of the depressions form an angle of inclination relative to the horizontal of about 30° maximum. Below the upper neck portion, the implant has a self-tapping thread, and the neck portion of the implant is provided with a porcelain-like coating. The surface energy, or "zeta potential", and the surface tension of the implant are kept as low as possible. Materials used for the implants are preferably titanium, titanium-based alloys or porcelain-like substances. The depressions are preferably designed as systematically trapezoid grooves extending parallel to one another, said grooves being generated mechanically.

By virtue of the invention, an implant is now available which, while providing sound immediate postoperative primary stability, is distinguished, on account of improved osseointegration in terms of the biological union of the bone and the implant surface, by an accelerated and increased load-bearing capacity in terms of secondary anchoring.

BRIEF DESCRIPTION OF THE ATTACHED DRAWING

FIG. 1 shows a diagrammatic cross section through the surface structure, according to the invention, of an intraosseous implant.

DETAILED DESCRIPTION OF THE INVENTION

The surface characteristics of the implant materials used have a crucial influence on the time course and intensity of osseointegration since the implant is in contact with the implant site via the implant surface, which is thus also a determining factor in how this contact develops and is maintained. In view of the importance of the implant surface for osseointegration, various surface structures have been proposed for achieving a maximum level of anchored contact between the implant surface and the bone surrounding the fitted implant. Extensive and repeated research at tissue level led to the recognition that implant surfaces provided with a degree of roughness have greater bone contact than is the case with smooth surfaces.

By contrast, little work has hitherto been done on the reaction of osteogenetic cells to the different surface microstructures. In particular, previous studies on the causal molecular relationships between the biological cell behavior and different surface structures have been very scanty. Since it is above all molecular factors that form the basis of cellular activity and tissue reaction, the invention is based on studies in this direction. In a newly created bone implant site, proteins and ions circulate and determine the cell reactions in the first minutes and hours. The later cell reaction is further influenced by the toxicity effect of the implanted material. The long-term reaction of the cells at the implant site to the presence of an implanted material is a response to the combination of the molecular reaction potential of the material and its toxic effect.

Series of tests revealed a marked difference in cell reaction between smoothly polished material surfaces and rough material surfaces (corundum-abraded and plasma-coated). On a smooth surface there is a higher level of cell growth, with cells proliferating in planar fashion, than there is on a rough implant surface. More fibronectin is adsorbed on a smooth surface and distributed over a wide area. On rough surfaces, fibronectin adsorption varies from negligible to undetectable. The cells on smooth specimens show filopodia and lamellopodia in multiple directions, whereas a large number of the cells on a rough surface have a spindle-shaped morphology. The influence of the surface structure of titanium on the behavior of fibroblasts in the proliferation, growth and formation of focal adhesions has already been the subject of investigation (cf. Könönen, M. et al.: "Effect of surface processing on the attachment, orientation and proliferation of human gingival fibroblasts on titanium" J. Biomed. Mater. Res. (26) 1325–1341, 1992). According to the above, fibroblasts also tend to adhere to and grow on smooth surfaces rather than rough ones. Focal adhesions were observed only in connection with smooth surfaces. In the case of chondrocytes too, relationships between flattening and growth detected on smooth surfaces were superior to those for rough surfaces.

Cell phenomenology is of course material-specific, but going beyond this it is determined by the surface microstructure. Steel and titanium are capable of comparable binding of fibronectin. This is corroborated by study results showing that in the cell culture the distribution of fibronectin and cell growth on smooth steel and titanium surfaces is comparable. On rough titanium surfaces, the corresponding fibronectin binding and cell growth was less marked. In correlation with the fibronectin distribution on the different titanium surfaces, the cell proliferation was more marked and monolayer development more advanced on smooth surfaces than on rough ones.

These results point to the hypothesis that the discrepancy in cell behavior between smooth and rough titanium surfaces is attributable to the topology/morphology of the surface below 10 $\mu$m, where 10 $\mu$m is the order of magnitude of the cell dimension. When a cell approaches a smooth surface, every point is potentially available for focal contact. In the case of a rough surface, by contrast, cell contact is possible only on the protruding areas. If there are no areas for formation of focal contacts, then cell adhesion and proliferation fail to materialize.

The series of tests carried out revealed that the roughest surfaces (plasma-coated and corundum-abraded and etched) are associated with the smallest amounts of adsorbed fibronectin; fibronectin is presumably adsorbed only at the limited places available for the cells. By contrast, larger areas were available on the smooth surfaces for the adsorption of the greater amounts of fibronectin detected. Also, cell migration was more extensive on rough surfaces than on smooth ones. This can be deduced in particular from the mode of movement of the cells. Cells which migrate long distances send out long explorative filopodia and are bipolar, whereas slowly moving cells have a multipolar appearance.

It was observed that the formation of fibronectin microfilaments was detectable only on polished steel and titanium surfaces; on rougher surfaces, actin was present in only negligible or undetectable amounts. This suggests that if focal adhesions are formed on rough surfaces, these have insufficient stability to support actin fiber formation. A comparison between these findings and the earlier studies is of fundamental importance. The earlier studies revealed that fibroblasts preferably adhere to and grow on smooth titanium surfaces rather than rough ones. Focal adhesions were observed only in connection with smooth surfaces (cf. Könönen, M., et al., loc. cit.). On smooth surfaces, compared to rough ones, chondrocytes also showed superior flattening and growth relationships.

The studies preparing the way for the invention provide an explanation for the behavior of fibroblasts and chondrocytes and for the fact that roughened surfaces in the cell dimension range have a disadvantageous effect on cell adhesion. By contrast, an implant surface which is as smooth as possible and in the cell dimension range promotes osseointegration.

Cell phenomenology, i.e. adhesion, proliferation and formation of attachments to substrates, has great importance for cell function and also for osseointegration of implants. The transfer of information to the cell interior is effected via cell/substrate attachments. In this connection, focal contacts serve for locomotion, and focal adhesions serve for flattening. Focal contacts are rectilinear structures with the dimension 0.25–0.5×2–10 μm which are broken up after 4 to 20 minutes. Focal adhesions are more stable in structure and over time and are spatially more extensive; they are a prerequisite for synthesis and deposition of extracellular matrix (cf. Woods, A., et al.: "Stages in specialization of fibroblast adhesion and deposition of extracellular matrix". Eur. J. Cell Biol. (32) 108–116, 1983). Only with flattening do the cells enter the DNA synthesis; cell rounding, by contrast, cancels DNA synthesis.

On the cell side of the focal adhesions, the cytoskeletal actin is organized—via vinculin, talin and cx-actinin—into bundles (stress fibers). This results especially in signal transduction from the substrate to the cell interior for synthesis of extracellular matrix. The substrate and focal adhesion complex then also regulates, via polyribosomes and mRNA, the rate of protein synthesis and the release of tissue-specific proteins.

These processes—thus the surface microstructure—are consequently of great importance for optimum incorporation and tissue integration of bone implants. The more the chemical properties and microstructure of the surface of a material permit the formation of focal adhesions and focal contacts, the more intensively is its biological integration (osseointegration) promoted. In principle, a bone implant surface with a rough micromorphology is desirable since in this way the surface and the potential contact between bone and implant are considerably increased. Although an enlarged surface area also results in increased release of disintegration particles, the increase in surface area obtained nevertheless increases the interaction potential and mechanical stability. However, the roughening must not fall below the dimension range of the cell.

There are cytophysical and molecular reasons why irregularities in the dimension range of the cell ought to have a disadvantageous effect on tissue integration. A cell cannot work its way into every corner in order to maintain a close relation with the substrate at all points, yet the close physical relationship between cell and substrate is imperative for morphogenesis. Moreover, microscopic elevations and depressions in this range lead to a reduction in cell adhesion if they do not satisfy the geometry and minimum dimension for formation of focal adhesions and focal contacts.

This also explains the non-optimum osseointegration of plasma-coated implant materials, where the plasma layer has islands of relatively smooth structure which ought not to reduce the formation of focal adhesions and focal contacts. However, the overall surface is for the most part uneven and thus presents, in particular in the cell dimension range, unfavorable conditions for the formation of focal adhesions and focal contacts. The commonly used acid etching of the implant surface results in a surface porosity where material substance, at least in the case of titanium, ought to be removed preferably at grain boundaries and on defined crystallographic orientations. Since the etching is also intracrystalline, porosities also form here in the cell dimension range which ought to be disadvantageous in the formation of focal adhesions and focal contacts. Corundum abrasion alone does not give any marked microporosities on the material surface. If corundum abrasion is followed by acid etching, micro depressions occur with a diameter of ca. 10 nm to 100 nm. However, these sizes lie outside the cell dimension range and do not adversely impair the formation of focal adhesions and focal contacts, provided that the micro craters are themselves smooth. However, like surfaces which are only acid-etched, those surfaces in the cell dimension range which are first corundum-abraded and then acid-etched are also rough and are therefore likewise unfavorable for cell adhesion.

In terms of cell mechanics, a cell moving along cannot change the direction of movement by more than an angle of 32°. Presumably the actin fibers which attach to the front margin of the cell in the focal contacts for cell movement and pull the rest of the cell can only pull directly and not round corners (cf. Dunn, G. A.; Heath, J. P.: "A new hypothesis of contact guidance in tissue cells". Exp. Cell Res. (101) 1–14, 1976). The cell can then refuse to move in this direction or in some circumstances bridge the gap with cell bodies or flagella. In a series of tests, this bridging action was found on polished and etched, plasma-coated and corundum-abraded and etched surfaces. However, in the case of unpolished calcium phosphate ceramics, but with no pronounced changes in relief in the dimensions of subcellular range, cell proliferation likewise takes place.

The fact that a cell cannot cover every uneven surface is probably also connected to the geometry and minimum dimension of the cell anchoring apparatus. Cells need focal contacts for their locomotion and focal adhesions for their anchoring and proliferation. A focal contact required for locomotion is 0.25 μm to 0.5 μm wide, and at least 2 μm long. Substrate irregularities of small dimension presumably do not permit the formation of these important anchoring structures. A cell for this reason does not dwell at a site with too small a dimension and instead leaves it to move to a surface of greater dimension.

Assuming that the morphogenetic activity of osteoblasts is influenced by the molecular and cellular laws discussed above, this would necessarily also have a bearing on the development of interface bone and thus on osseointegration. The surface chemistry and the surface micromorphology ought to represent the principal material parameters. Implant surfaces which can bind to them the critical molecules for bone union and morphogenesis promise a greater rate of implantation success, particularly in the long term. Given the requirements in respect of the specific surface and also the interface cell activity, a surface micromorphology with depressions of 20 μm to about 60 μm is therefore viable. Plane zones should have a horizontal extent of 10 μm to about 20 μm. The depressions are ideally as smooth as possible and angles at the implant surface are about 30° maximum. The surface energy (zeta potential) and the surface tension should be kept as low as possible. A porcelain-like coating would be ideal on the implant neck.

PREFERRED ILLUSTRATIVE EMBODIMENT

Referring to attached FIG. 1, we will now describe a preferred illustrative embodiment. The implant surface has a multiplicity of depressions 1. At the bottom of the depressions 1 there are base faces 2, and extending between the depressions 1 there are plateau faces 3. Ascending side faces 4 extend upward from the base faces 2 to the plateau faces 3. The depressions 1 have a depth c measured vertically between the plateau faces and base faces 3, 2 of about 20 μm to about 60 μm. The base faces 2 have a horizontal extent a which amounts to about 10 μm to about 20 μm in width. The horizontal extent b of the plateau faces 3 likewise amounts to about 10 μm to about 20 μm in width. The base faces and plateau faces 2, 3 are infinite in length when the depressions 1 extend radially about the implant. The depressions 1 and the plateau faces 3 are ideally made as smooth as possible by polishing, that is to say they have no surface roughness below the cellular dimension.

The side faces 4 of the depressions 1 form an angle of inclination α relative to the horizontal of about 30° maximum. The depressions 1 are preferably designed as systematically trapezoid grooves extending parallel to one another and are mechanically generated by removal of material or stamping.

What is claimed is:

1. An intraosseous implant having an implant surface which is provided with a specific roughness in order to promote the load-bearing capacity of the implant, the implant surface having a multiplicity of depressions and a multiplicity of plateau faces arranged between the depressions, wherein the depressions have a bottom with a base face and with side faces extending from the bottom of the depressions to the plateau faces, each of the base faces and each of the plateau faces having a horizontal extent of 10 μm to 20 μm, and each of the depressions having a vertically measured depth of 20 μm to 60 μm, and wherein further the depressions and the plateau faces are smooth.

2. The implant of claim 1, wherein each of the side faces of the depressions form an angle of inclination relative to the horizontal no greater than about 30°.

3. The implant of claim 1, wherein the implant is made of titanium.

4. The implant of claim 1, wherein the implant is made of a titanium-based alloy.

5. The implant of claim 1, wherein the implant is made of a porcelain-like substance.

6. The implant of claim 1, wherein the depressions are systematically arranged trapezoid grooves extending parallel to one another, with the plateau faces lying between the trapezoid grooves.

7. The implant of claim 6, wherein the horizontal extent of each of the base faces refers to the width of each of the trapezoid grooves, and the horizontal extent of each of the plateau faces refers to the width of the each of the plateau faces between the trapezoid grooves.

8. The implant of claim 1, wherein the depressions are mechanically generated.

* * * * *

UNITED STATES PATENT AND TRADEMARK OFFICE
CERTIFICATE OF CORRECTION

PATENT NO. : 6,554,867 B1
APPLICATION NO. : 09/869781
DATED : April 29, 2003
INVENTOR(S) : Ulrich Joos Page 1 of 1

It is certified that error appears in the above-identified patent and that said Letters Patent is hereby corrected as shown below:

In the Specification:

Column 2, lines 51-67 should be deleted in their entirety.

Column 3, lines 1-14 should be deleted in their entirety.

Signed and Sealed this
Twenty-fifth Day of June, 2013

Teresa Stanek Rea
*Acting Director of the United States Patent and Trademark Office*